(12) United States Patent
Chang et al.

(10) Patent No.: US 12,730,169 B2
(45) Date of Patent: Sep. 8, 2026

(54) DYNAMIC LOW-ORDER SHIMMING FOR ARTERIAL SPIN LABELING

(71) Applicants: Siemens Healthineers AG, Forchheim (DE); The General Hospital Corporation, Boston, MA (US)

(72) Inventors: Yulin Chang, Belmont, MA (US); Meher Juttukonda, Boston, MA (US); Jason Stockmann, Cambridge, MA (US)

(73) Assignees: Siemens Healthineers AG, Forchheim (DE); The General Hospital Corporation, Boston, MA (US)

( * ) Notice: Subject to any disclaimer, the term of this patent is extended or adjusted under 35 U.S.C. 154(b) by 196 days.

(21) Appl. No.: 18/798,972

(22) Filed: Aug. 9, 2024

(65) Prior Publication Data

US 2025/0275683 A1 Sep. 4, 2025

Related U.S. Application Data

(60) Provisional application No. 63/559,985, filed on Mar. 1, 2024.

(51) Int. Cl.

*G01R 33/3875* (2006.01)
*A61B 5/00* (2006.01)

(Continued)

(52) U.S. Cl.

CPC .......... *G01R 33/3875* (2013.01); *A61B 5/055* (2013.01); *A61B 5/742* (2013.01);

(Continued)

(58) Field of Classification Search

CPC .............. G01R 33/3875; G01R 33/543; G01R 33/56366; A61B 5/055; A61B 5/742

See application file for complete search history.

(56) References Cited

U.S. PATENT DOCUMENTS

2017/0089996 A1* 3/2017 Feiweier .............. G01R 33/583
2021/0235681 A1 8/2021 Chew et al.

(Continued)

OTHER PUBLICATIONS

Craven-Brightman, L., Chang, Y., Witzel, T., Arango, N. S., Juttukonda, M. R., Hernandez-Garcia, L., . . . & Stockmann, J. (2021). Regulating labeling efficiency in arterial spin labeling using a multi-coil B0 shim array: Application to territory mapping. (Year: 2021).*

(Continued)

*Primary Examiner* — Keith M Raymond
*Assistant Examiner* — Johnathan Maynard

(57) ABSTRACT

Systems and methods include executing a labeling phase of a pulse sequence while respective first shim currents are applied to first-order shim coils, respective second shim currents are applied to second-order shim coils, and a center frequency of an RF system is set to a first center frequency, switching, during a post-labeling delay of the pulse sequence, the first shim currents to third shim currents and the center frequency of the RF system to a second center frequency, executing a readout phase of the pulse sequence to acquire first MR data from an imaging volume of a subject while the respective third shim currents are applied, the respective second shim currents are applied s, and the center frequency is set to the second center frequency, and generating an image based on the first MR data.

17 Claims, 6 Drawing Sheets

(51) Int. Cl.
*A61B 5/026* (2006.01)
*A61B 5/055* (2006.01)
*G01R 33/54* (2006.01)
*G01R 33/563* (2006.01)

(52) U.S. Cl.
CPC ..... *G01R 33/543* (2013.01); *G01R 33/56366* (2013.01); *A61B 5/0263* (2013.01); *A61B 5/7203* (2013.01); *A61B 2576/00* (2013.01)

(56) References Cited

U.S. PATENT DOCUMENTS

2022/0304582 A1* 9/2022 Chang .................. A61B 5/0263
2024/0237910 A1* 7/2024 Lee .................. G01R 33/56581

OTHER PUBLICATIONS

Hirschler, L., Debacker, C. S., Voiron, J., Köhler, S., Warnking, J. M., & Barbier, E. L. (2018). Interpulse phase corrections for unbalanced pseudo-continuous arterial spin labeling at high magnetic field. Magnetic Resonance in Medicine, 79(3), 1314-1324. (Year: 2018).*

Woods et al. "Minimizing SAR for SNR-Efficient pseudo-continuous arterial spin labeling at 7T", ISMRM 2023;0371.

Ghariq, Eidrees, et al. "Feasibility of pseudocontinuous arterial spin labeling at 7 T with whole-brain coverage." Magnetic Resonance Materials in Physics, Biology and Medicine 25.2 (2012): 83-93.

Sengupta, Saikat, et al. "Dynamic B0 shimming at 7 T." Magnetic resonance imaging 29.4 (2011): 483-496.

Van Gelderen, Peter, et al. "Real-time shimming to compensate for respiration-induced B0 fluctuations." Magnetic Resonance in Medicine: An Official Journal of the International Society for Magnetic Resonance in Medicine 57.2 (2007): 362-368.

Craven-Brightman, Lincoln, et al. "Regulating labeling efficiency in arterial spin labeling using a multi-coil B0 shim array: Application to territory mapping." (2021).

EP Search Report in EP Application No. 25160152.2, dated Jul. 29, 2025, 6 pages.

Aguirre et. al.: "Experimental design and the relative sensitivity of BOLD and perfusion fMRI." Neuroimage. Mar. 2002; 15(3):488-500. doi: 10.1006/nimg.2001.0990. PMID: 11848692.

Zhang, X. (Jan. 31, 2019). "Expanding the capabilities of arterial spin labeling MRI." Retrieved from https://hdl.handle.net/1887/68471.

Boland, Markus, et al. "Robust and SAR-efficient whole-brain pseudo-continuous ASL at 7T." Proceedings of the 27th Annual Meeting of ISMRM, Montreal, Canada. 2019.

Yang Ji, et. al.: "Dynamic B0 field shimming for improving pseudo-continuous arterial spin labeling at 7 Tesla" bioRxiv 2024.07.22.604544; doi: https://doi.org/10.1101/2024.07.22.604544.

Meixner et. al.: "Hybrid B+-shimming and gradient adaptions for improved pseudo-continuous arterial spin labeling at 7 Tesla", Magnetic Resonance in Medicine May 2021.

Buxton, Richard B. "Quantifying CBF with arterial spin labeling." Journal of Magnetic Resonance Imaging: An Official Journal of the International Society for Magnetic Resonance in Medicine 22.6 (2005): 723-726.

Morrell, Glen, and Daniel Spielman. "Dynamic shimming for multi-slice magnetic resonance imaging." Magnetic resonance in medicine 38.3 (1997): 477-483.

May, Markus W., et al. "A patient-friendly 16-channel transmit/64-channel receive coil array for combined head-neck MRI at 7 Tesla." Magnetic resonance in medicine 88.3 (2022): 1419-1433.

Berry,Eleanor S.K. et. al. "Off-resonance correction for pseudo-continuous arterial spin labeling using the optimized encoding scheme", NeuroImage, vol. 199, 2019, pp. 304-312, ISSN 1053-8119,https://doi.org/10.1016/j.neuroimage.2019.05.083.

Wang, Kai, et al. "Optimization of pseudo-continuous arterial spin labeling at 7T with parallel transmission B1 shimming." Magnetic resonance in medicine 87.1 (2022): 249-262.

Jahanian, Hesamoddin; Noll, Douglas C.; Hernandez-garcia, Luis (2011). "B0 field inhomogeneity considerations in pseudoa continuous arterial spin labeling (pCASL): effects on tagging efficiency and correction strategy." NMR in Biomedicine 24(10): 1202-1209. <http://hdl.handle.net/2027.42/89456>.

Dai, Weiying, et al. "Continuous flow-driven inversion for arterial spin labeling using pulsed radio frequency and gradient fields." Magnetic Resonance in Medicine: An Official Journal of the International Society for Magnetic Resonance in Medicine 60.6 (2008): 1488-1497.

Hess, Aaron T., et al. "Real-time motion and B0 corrected single voxel spectroscopy using volumetric navigators." Magnetic resonance in medicine 66.2 (2011): 314-323.

Shin, David D., et al. "Pseudocontinuous arterial spin labeling with optimized tagging efficiency." Magnetic resonance in medicine 68.4 (2012): 1135-1144.

Luh, Wen-Ming, et al. "Pseudo-continuous arterial spin labeling at 7T for human brain: estimation and correction for off-resonance effects using a Prescan." Magnetic Resonance in Medicine 69.2 (2013): 402-410.

Alsop, David C., et al. "Arterial spin labeling blood flow MRI: its role in the early characterization of Alzheimer's disease." Journal of Alzheimer's Disease 20.3 (2010): 871-880.

Stafford, Randall B., et al. "An actively decoupled dual transceiver coil system for continuous ASL at 7T." International journal of imaging systems and technology 26.2 (2016): 106-115.

Zhao, Li, et al. "Improving the robustness of pseudo-continuous arterial spin labeling to off-resonance and pulsatile flow velocity." Magnetic resonance in medicine 78.4 (2017): 1342-1351.

Saïb, Gaël, Alan P. Koretsky, and S. Lalith Talagala. "Optimization of pseudo-continuous arterial spin labeling using off-resonance compensation strategies at 7T." Magnetic resonance in medicine 87.4 (2022): 1720-1730.

Detre, John A., and David C. Alsop. "Perfusion magnetic resonance imaging with continuous arterial spin labeling: methods and clinical applications in the central nervous system." European journal of radiology 30.2 (1999): 115-124.

Kim SG. "Quantification of relative cerebral blood flow change by flow-sensitive alternating inversion recovery (FAIR) technique: application to functional mapping". Magn Reson Med. Sep. 1995;34(3):293-301. doi: 10.1002/mrm.1910340303. PMID: 7500865.

* cited by examiner

DYNAMIC LOW-ORDER SHIMMING FOR ARTERIAL SPIN LABELING

CROSS-REFERENCE TO RELATED APPLICATIONS

The present application claims the benefit of, and priority to, U.S. Provisional Patent Application No. 63/559,985, filed Mar. 1, 2024, the contents of which are incorporated herein by reference for all purposes.

BACKGROUND

Magnetic Resonance (MR) imaging uses magnetic fields and radio-frequency (RF) pulses to non-invasively image organs, tissues and the physiological processes of the body. Arterial spin labeling (ASL) is a particular MR imaging technique for evaluating tissue perfusion. According to ASL, water nuclei in the blood are RF labeled before the blood perfuses into tissue, and k-space signals are acquired from the tissue while the RF-labeled blood is present in the tissue. Images are generated based on the k-space signals and blood perfusion within the tissue may be evaluated based on the images.

Several types of ASL techniques exist. In pulsed ASL (PASL), blood surrounding the imaging volume is labeled using a single pulse which defines the volume of arterial blood to be labeled. In continuous ASL (CASL) and pseudo-continuous ASL (pCASL), blood located upstream of the imaging volume is continuously inverted or saturated as it passes a particular plane.

pCASL uses a narrow labeling plane through which a long train of short, Hanning-windowed block RF pulses causes flow-related adiabatic inversion of arterial spins. The labeling plane is usually located immediately upstream of the imaging volume, which minimizes signal loss from the decay of the thusly-labeled blood. pCASL is the most widely used ASL implementation because it affords high labeling efficiency (i.e., Signal-to-Noise Ratio).

Since excitation RF pulses are applied to both the labeling region and the imaging volume, ASL is susceptible to off-resonance of the $B_0$ magnetic field in the labeling region as well as in the imaging volume. Off-resonance of the $B_0$ magnetic field within the imaging volume may cause image artifacts such as blurring, signal dropout, and geometric distortion. Similarly, off-resonance in the labeling plane can significantly reduce the labeling efficiency.

The presence of off-resonant $B_0$ fields in the labeling plane is common in pCASL because the labeling plane is outside of the imaging volume and the MR scanner shim currents are calculated to prioritize maintaining $B_0$ field homogeneity within the imaging volume as opposed to the labeling plane. As a result, the labeling plane may exhibit $B_0$ off-resonance. The $B_0$ off-resonance in the labeling plane can be exacerbated by any shimming of the imaging volume, which may lead to unwanted magnetic field changes in the labeling plane. $B_0$ off-resonance in the labeling plane can also be caused by the presence of magnetic materials near the labeling plane such as dental implants. If left unaddressed, $B_0$ off-resonance in the labeling plane results in varying labeling efficiencies between subjects and between scans, and ultimately results in inconsistent and incorrect blood perfusion measurement.

Prior attempts to address the foregoing include a calibration scan to identify off-resonance in the labeling plane and/or adding a phase factor to the labeling RF pulse, independently or in combination with the optimization of the gradient pulses, to improve labeling efficiency. Recently, a method was proposed that attempts to optimize $B_1$ and gradient fields in unbalanced pCASL (ubpCASL) to improve the labeling efficiency for off-resonance blood. None of these methods directly addresses the underlying problem of $B_0$ field off-resonance in the labeling plane.

Systems to efficiently achieve $B_0$ resonance in the labeling plane and in the imaging volume during ASL imaging are desired.

DETAILED DESCRIPTION

Figure 1:
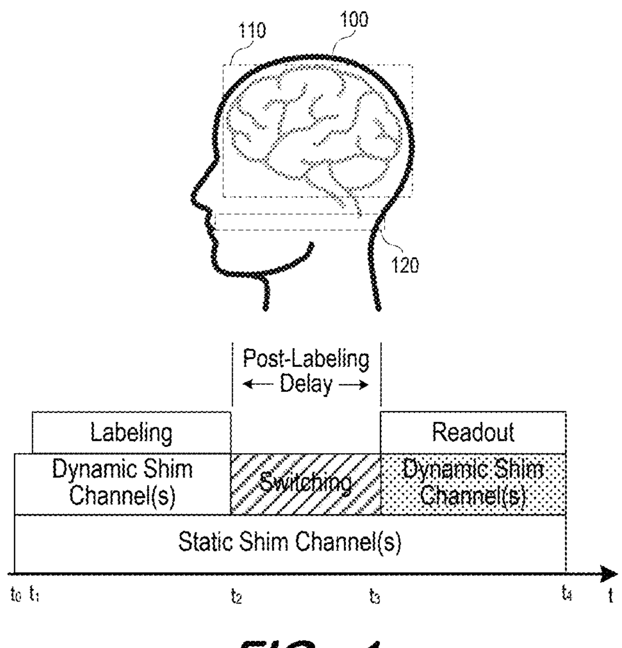
FIG. 1 illustrates dynamic shimming of a labeling region and an imaging volume according to some embodiments.

The following description is provided to enable any person in the art to make and use the described embodiments. Various modifications, however, will remain readily apparent to those in the art.

Shimming refers to the process of reducing the effects of $B_0$ field inhomogeneity and/or off-resonance. Conventionally, shimming includes detection of inhomogeneities within a $B_0$ field and decomposition of the inhomogeneities into spatial field variations of $0^{th}$-, $1^{st}$-, $2^{nd}$-, $3^{rd}$-, and potentially higher-order spherical harmonics. The $0^{th}$-order harmonic includes one term (i.e., component), the $1^{st}$-order harmonic includes three components (e.g., X, Y, Z), the $2^{nd}$-order harmonic includes five components, and the $3^{rd}$-order harmonic includes seven components.

For each unwanted spherical harmonic component of the $1^{st}$-order or higher, a supplemental magnetic field is generated which is intended to exhibit the same spatial distribution as, but be equal and opposite to, the unwanted component. Each thusly-generated supplemental magnetic field is therefore intended to cancel the unwanted spherical harmonic component to which it corresponds.

The supplemental magnetic fields are generated by passing current through a resistive coil. Accordingly, a standard shimming implementation consists of a set of coils, in which each coil generates a supplemental magnetic field for addressing a particular unwanted spherical harmonic component in response to direct current passed therethrough. The currents which are passed through the shim coils in order to generate the supplemental fields are referred to as shim currents and may be calculated as is known in the art.

Each shim coil may be driven by an individual shim power supply. A shim coil may be physically separate from the MR scanner or incorporated into the gradient coil structure. In some implementations the main X, Y and Z gradient coils simultaneously act as $1^{st}$-order shim coils, e.g., via the addition of DC shim current offsets to the gradient currents.

The $0^{th}$-order shim channel may comprise components to adjust a center frequency of RF pulses and received signals. Both the center frequency and the shim currents of the $1^{st}$-order shim channels may be switched from one steady state to another within a short amount of time (e.g., ~1s). This $0^{th}$-order and $1^{st}$-order shim channels will be referred to as "dynamic" shim channels while other shim channels will be referred to as "static" shim channels.

According to some embodiments, the static shim channels and the dynamic shim channels of an MR scanner are operated to reduce $B_0$ off-resonance in a labeling region during a labeling period. In some embodiments, shimming during a labeling period includes adjusting the center frequency of the RF pulses used during a labeling phase and adjusting the shim currents applied to the $1^{st}$-order shim channels to account for off-resonance in the labeling region caused by the shim currents applied to the static shim channels. After the labeling period, the center frequency of the RF pulses and the shim currents applied to the $1^{st}$-order shim channels return to their default values suited for imaging the imaging volume Consequently, labeling efficiency can be improved due to a reduction in $B_0$ off-resonance in the labeling plane during labeling, and image quality is maintained by reducing $B_0$ inhomogeneity and off-resonance in the imaging volume during readout.

Unlike the approaches described above, some embodiments do not require updating the phase of the RF pulse or the gradient strength to address $B_0$ off-resonance in the labeling plane, and thus can be more easily executed in a clinical setting. Some embodiments also do not require separate shim coil arrays near the labeling region, but rather may utilize only shim channels provided by the MR scanner.

FIG. 1 illustrates dynamic shimming of a labeling region and an imaging volume according to some embodiments. It will be assumed that subject 100 of FIG. 1 is disposed within the bore of an MR scanner at time to. Subject 100 is to be subjected to an MR pulse sequence in order to acquire k-space data from imaging volume 110 which includes the brain. Embodiments are not limited to this imaging volume or to a single imaging volume. The example below will describe a pCASL pulse sequence, but embodiments are also not limited thereto.

FIG. 1 also shows labeling region 120, which may comprise a plane or a volume. A location of labeling region 120 is selected to ensure that molecules labeled in that region flow to imaging volume 110 shortly after such labeling. Embodiments are not limited to the location of labeling region 120 or to one labeling region.

One or more static shim channels and one or more dynamic shim channels are operated beginning at time to. For example, shim currents are applied to coil-based shim channels and a center RF frequency is adjusted. Next, a labeling phase of a pulse sequence is executed from time $t_1$ to time $t_2$ to label molecules in labeling region 120 while the shim currents and center frequency are maintained. The shim currents and frequency adjustment applied from time $t_1$ to time $t_2$ are pre-determined to reduce $B_0$ off-resonance in labeling region 120 during the labeling phase.

A post-labeling delay elapses between time $t_2$ and time $t_3$. This post-labeling delay is known in the art of pCASL sequences and is intended to allow the now-labeled molecules to flow to imaging volume 110. The post-labeling delay may comprise any suitable length of time. The shim currents applied to the static shim channels remain constant during the post-labeling delay. However, the dynamic shim channels are switched to a new state during the post-labeling delay. This new state may include new shim currents for the $1^{st}$-order shim channels and a new center frequency for the $0^{th}$-order shim channel. It is assumed that, by $t_3$, any change to the $1^{st}$-order shim currents and center frequency has been effected and has stabilized.

From time $t_3$ to time $t_4$, the original shim currents applied to the static shim channels at time to remain unchanged, the $1^{st}$-order shim channels carry new shim currents the and $0^{th}$-order shim channel is set to a new center frequency. The center frequency and shim currents used between time $t_3$ and time $t_4$ are intended to reduce $B_0$ off-resonance and inhomogeneities within imaging volume 110 during this time period. Accordingly, between time $t_3$ and time $t_4$, the MR scanner applies readout pulses suitable to readout signals from imaging volume 110. The readout pulses may comprise an echo-planar imaging pulse sequence, a fast spin echo pulse sequence, a gradient-recalled echo pulse sequence, or any other suitable pulse sequence.

An image may be generated based on the signals acquired from imaging volume 110 during the readout phase as is known in the art. The image may be compared with an image generated using the readout pulse sequence, shim currents and center frequency described above with respect to the readout phase but without a preceding labeling phase. Some embodiments include generation of a unitless perfusion-weighted image based on a difference between the two images.

Figure 2:
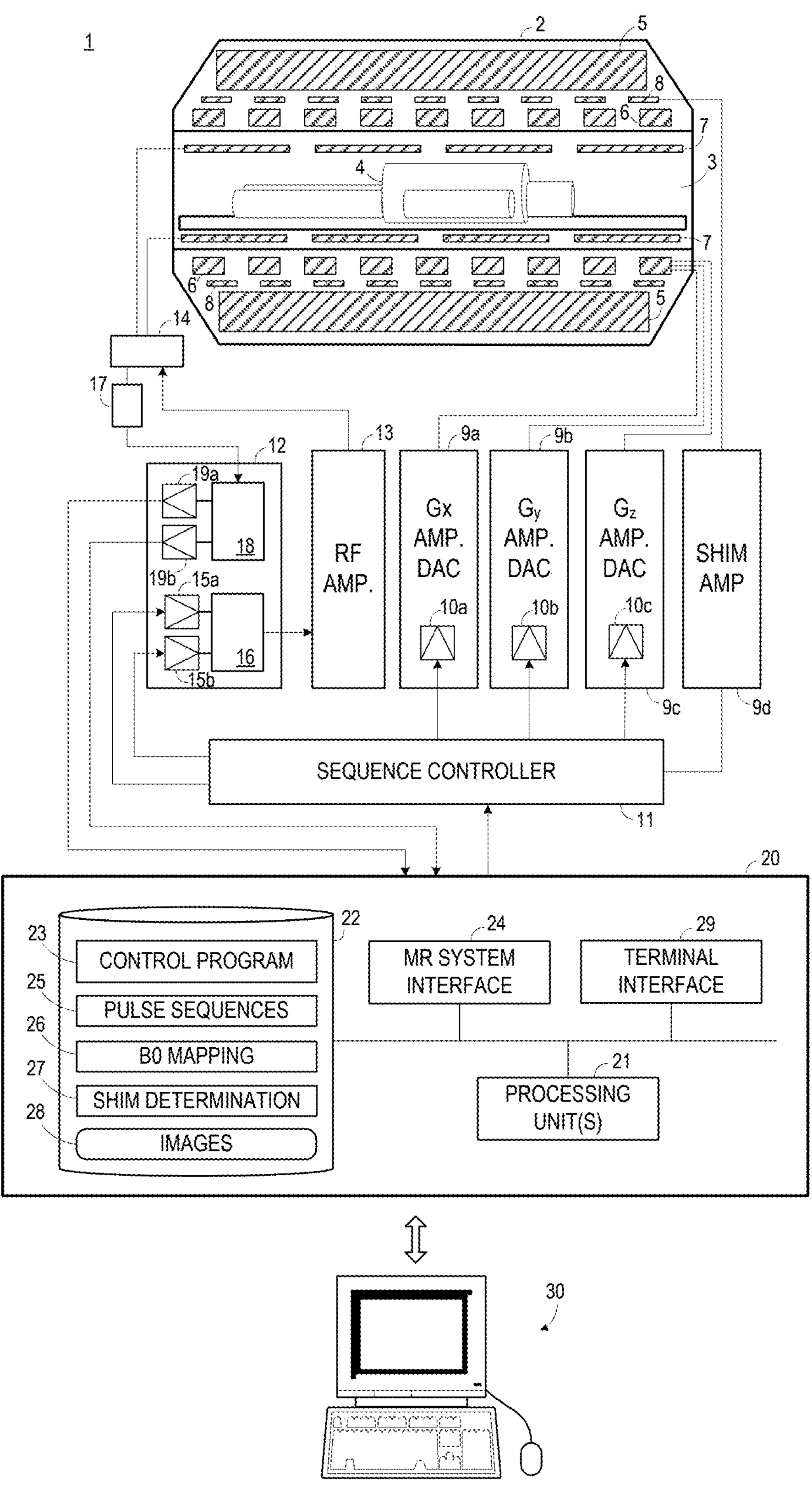
FIG. 2 is a block diagram of an MR imaging system according to some embodiments.

FIG. 2 is a block diagram of MR imaging system 1 for executing pulse sequences to acquire k-space data and reconstructing images therefrom according to some embodiments. Embodiments are not limited to MR system 1.

In MR imaging, a volume of material (e.g., human tissue) is subjected to a main polarizing magnetic field (i.e., $B_0$). The field causes the individual magnetic moments of the nuclear spins in the substance to process about the polarizing field in random order at their characteristic Larmor frequency, in an attempt to align with the field. A net magnetic moment $M_z$ is produced in the direction of the polarizing field, and the randomly oriented magnetic components in the perpendicular plane (the x-y plane) cancel out one another.

The material is then subjected to an excitation field (i.e., $B_1$) created by emission of an RF pulse, which is in the x-y plane and near the Larmor frequency, causing the net aligned magnetic moment $M_z$ to rotate into the x-y plane so as to produce a net transverse magnetic moment $M_t$, which is rotating, or spinning, in the x-y plane at the Larmor frequency. The excitation field is terminated, and signals are emitted by the excited spins as they return to their pre-excitation field state. The emitted signals (i.e., k-space data) are detected, digitized and processed to reconstruct an image using one of many well-known MR reconstruction techniques.

MR system 1 includes MR chassis 2, which defines bore 3 in which subject 4 is disposed. MR chassis 2 includes polarizing main magnet 5, gradient coils 6 and RF coils 7 arranged about bore 3. According to some embodiments, polarizing main magnet 5 generates a main magnetic field ($B_0$) and RF coils 7 emit an excitation field ($B_1$). As mentioned above, in some embodiments an $0^{th}$-order shim channel includes RF coils 7 and other components used to apply emit RF pulses and detect the resulting signals at a predetermined center frequency.

Gradient coils 6 produce magnetic field gradients $G_x$, $G_y$, and $G_z$ which are used for position-encoding MR signals. The magnetic field gradients $G_x$, $G_y$, and $G_z$ distort the main magnetic field in a predictable way so that the Larmor frequency of nuclei within the main magnetic field varies as a function of position. Accordingly, an excitation field $B_1$ which is near a particular Larmor frequency will tip the net aligned moment $M_z$ of those nuclei located at field positions which correspond to the particular Larmor frequency, and signals will be emitted only by those nuclei after the excitation field $B_1$ is terminated.

Gradient coils 6 may consist of three windings, for example, each of which is supplied with current by a respective power amplifier 9*a*-9*c* in order to generate a linear gradient field in its respective Cartesian direction (i.e., x, y, or z). Each amplifier 9*a*-9*c* includes a digital-analog converter 10*a*-10*c* which is controlled by sequence controller 11 to generate desired gradient pulses at proper times. Gradient coils 6 may simultaneously serve as the $1^{st}$-order shim channels as described above. Advantageously, the strength of power amplifiers 9*a*-9*c* may facilitate fast switching of shim currents to these shim channels.

MR system 1 includes shim coils 8 disposed around bore 3 in between gradient coils 8 and main magnet 5. Embodiments are not limited to this arrangement of shim coils 8. Sequence controller 11 controls shim power amplifier 9*d* to provide desired shim currents to shim coils 8. The shim currents are intended to adjust the $B_0$ field at particular locations (e.g., a labeling region, an imaging volume) to correct for inhomogeneities and/or off-resonances. Shim power amplifier 9*d* is typically significantly less powerful than power amplifiers 9*a*-9*c* and therefore the shim currents applied to shim coils 8 typically cannot be switched quickly in a reliable manner.

Shim coils 8 may comprise superconducting and/or resistive shim coils which provide $2^{nd}$-order shimming, $3^{rd}$-order shimming, etc. Embodiments may also or alternatively utilize local shim components (e.g., shim coil arrays) placed near or on subject 4 and/or shim inserts inserted into bore 3 (e.g., very high-order shim (VHOS) insert for the brain) as is known in the art.

Local shim components and shim inserts typically exhibit low inductance and therefore may be switched to a stable state and turned off quickly. Accordingly, such components may be considered dynamic shim channels and are particularly suited for dynamic switching during a pulse sequence as described herein. Slower-switching components such as shim coils 8 may be considered static shim channels that are energized with fixed static shim currents during both the labeling and readout phases, with the shim currents applied to the faster-switching dynamic shim channels being dynamically changed between the labeling and readout phases as needed to establish the desired $B_0$ field profiles.

Examples of local shim components include a local cranial/brain shim coil device and a cervical/neck shim coil device. A local cranial/brain shim coil device may comprise a wearable coil device that includes an array of shim coils and a housing body that can be wrapped, molded, placed, worn, or otherwise temporarily affixed to a patient's head such that the coils partially surround the brain while the patient is located in a bore of an MR scanner.

The coils may be integrated into a flexible wrap-around body or rigidly coupled to a helmet body worn by the patient. The coils may include at least a subset of coils that extend below the brain to allow labeling of arterial blood in a labeling region (e.g., in the cervical region). The coils may include an array of 32 seven-turn coils that are arranged three-dimensionally around the patient's brain in close proximity to (or touching) the patient's head when worn.

A cervical/neck shim coil device is also a wearable device that includes an array of shim coils and a body. The body can be constructed similar to a cervical collar stabilization device, allowing the cervical/neck shim coil device to be rigidly affixed to a patient's neck area. Such a device may be worn on the back of the patient's head, making it more comfortable than a stabilization device. The shim coils of a cervical/neck shim coil device may include an array of twelve seven-turn coils that are arranged three-dimensionally around the patient's cervical region in close proximity to (or touching) the patient's neck worn.

Each direct current shim coil in a coil array may be considered a static shim channel as described herein. Applying direct current to the coils allows manipulation of the $B_0$ field created by the main MR magnet to improve homogeneity or to reduce off-resonance in desired regions as described herein.

Sequence controller 11 also controls the generation of RF pulses by RF system 12 and RF power amplifier 13. RF system 12 and RF power amplifier 13 are responsive to a scan prescription and direction from sequence controller 11 to produce RF pulses of the desired center frequency, phase, and pulse amplitude waveform. The generated RF pulses may be applied to each of RF coils 7. RF coils 7 convert the RF pulses emitted by RF power amplifier 13, via multiplexer 14, into a magnetic alternating field in order to excite the nuclei and align the nuclear spins of the object to be examined or the region of the object to be examined. RF pulses may be emitted in a magnetization preparation step in order to enhance or suppress certain signals.

The RF pulses are represented digitally as complex numbers. Sequence controller 11 supplies these numbers in real and imaginary parts to digital-analog converters 15*a*-15*b* in RF system 12 to create corresponding analog pulse sequences. Transmission channel 16 modulates the pulse sequences with a radio-frequency carrier signal having a base frequency corresponding to the resonance frequency of the nuclear spins in the volume to be imaged.

RF coils 7 both emit radio-frequency pulses as described above and receive the alternating field which is produced as a result of precessing nuclear spins, i.e., the nuclear spin echo signals. The received signals are received by multiplexer 14, amplified by RF amplifier 17 and demodulated in receiving channel 18 of RF system 12 in a phase-sensitive manner. Analog-digital converters 19*a* and 19*b* convert the demodulated signals into real and imaginary components.

Computing system 20 receives the real and imaginary components from analog-digital converters 19*a* and 19*b* and may process the components according to known techniques. Such processing may, for example, reconstructing two-dimensional or three-dimensional images by performing a Fourier transformation of k-space data, performing other image reconstruction techniques such as iterative or back-projection reconstruction techniques, applying filters to raw k-space data or to reconstructed images, generating functional magnetic resonance images, calculating motion or flow images, and generating a chemical shift vs. magnitude spectrum.

System 20 may comprise any general-purpose or dedicated computing system. Accordingly, system 20 includes one or more processing units 21 (e.g., processors, processor cores, execution threads, etc.) configured to execute processor-executable program code to cause system 20 to operate as described herein, and storage device 22 for storing the program code. Storage device 22 may comprise one or more fixed disks, solid-state random-access memory, and/or removable media (e.g., a thumb drive) mounted in a corresponding interface (e.g., a USB port).

Storage device 22 stores program code of control program 23. One or more processing units 21 may execute control program 23 to provide instructions to sequence controller 11 via MR system interface 24. For example, sequence controller 11 may be instructed to initiate a desired pulse sequence of pulse sequences 25, such as a pCASL pulse sequence according to some embodiments. In particular, sequence controller 11 may be instructed to control the switching of magnetic field gradients via amplifiers 9*a*-9*d* at appropriate times, the transmission of radio-frequency pulses having a specified center frequency, phase and amplitude at specified times via RF system 12 and RF amplifier 13, and the readout of the resulting MR signals.

Storage device 22 stores program code of $B_0$ mapping component 26 and shim determination component 27. $B_0$ mapping component 26 may implement known algorithms executable to evaluate the $B_0$ field within a given volume of subject 4. Relatedly, shim determination component 27 may comprise program code executable to utilize the output of $B_0$ mapping component 26 to determine shim currents and a center frequency for shimming during a labeling phase and shim currents and a center frequency for shimming during a readout phase as described herein.

Images 28 of subject 4 may be generated conventionally and/or as described herein. Images 28 may be provided to terminal 30 via terminal interface 29 of system 20. Terminal interface 29 may also receive input from terminal 30, which may be used to provide commands to control program 23 in order to control sequence controller 11 and/or other elements of system 1. The commands may include commands to specify a labeling region and an imaging volume and commands to initiate a pulse sequence to acquire image data of a subject. Terminal 30 may simply comprise a display device and an input device coupled to system 20. In some embodiments, terminal 30 is a separate computing device such as, but not limited to, a desktop computer, a laptop computer, a tablet computer, and a smartphone.

Each element of system 1 may include other elements which are necessary for the operation thereof, as well as additional elements for providing functions other than those described herein. Storage device 22 may also store data and other program code for providing additional functionality and/or which are necessary for operation of system 20, such as device drivers, operating system files, etc.

Figure 3:
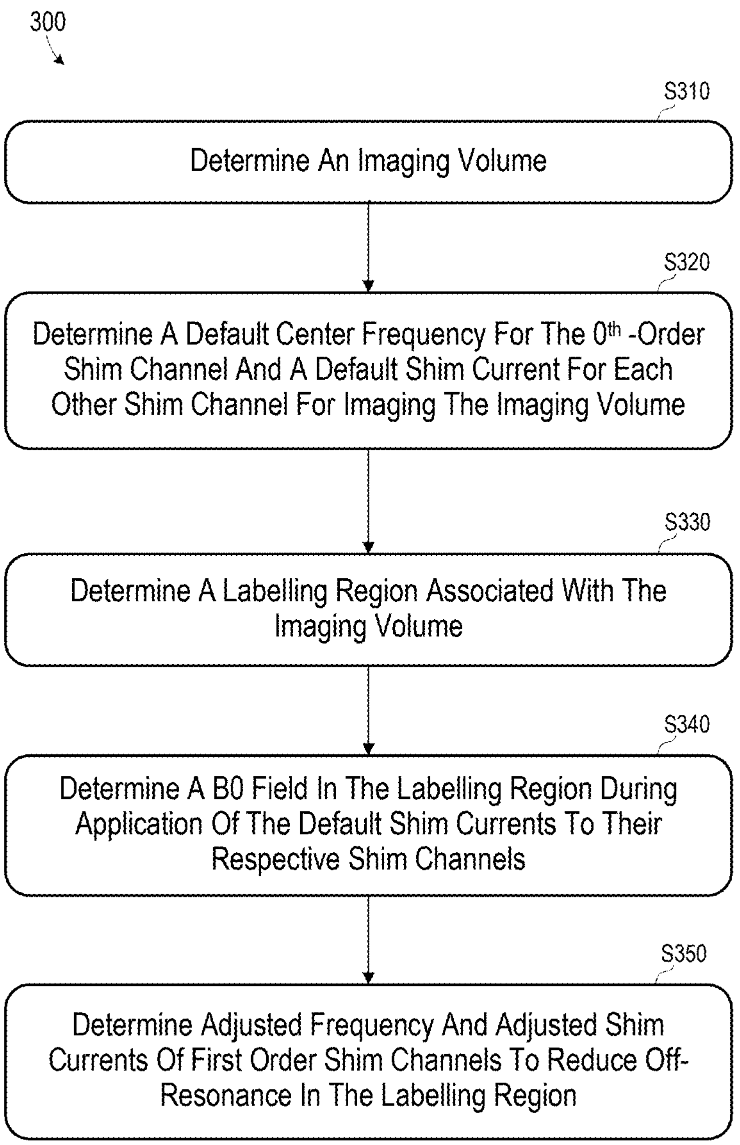
FIG. 3 is a flow diagram of a process to determine dynamic low-order shimming parameters for an arterial spin labeling sequence according to some embodiments.

FIG. 3 comprises a flow diagram of process 300 to dynamically shim a labeling region and an imaging volume according to some embodiments. Process 300 may be executed by various components of MR system 1, but embodiments are not limited thereto. In some embodiments, various hardware elements (e.g., one or more processing units) execute program code to perform process 300. The steps of process 300 need not be performed by a single device or system, nor temporally adjacent to one another.

Process 300 and all other processes mentioned herein may be embodied in program code read from one or more of non-transitory computer-readable media, such as a disk-based or solid-state hard drive, a DVD-ROM, a Flash drive, and a magnetic tape, and executed by one or more processing units (e.g., processors, processor cores, processor threads). In some embodiments, hard-wired circuitry may be used in place of, or in combination with, program code for implementation of processes according to some embodiments. Embodiments are therefore not limited to any specific combination of hardware and software.

Initially, an imaging volume is determined at S310. S310 may include acquisition of a localizer, or scout, image of a subject by an MR scanner in which the subject is disposed. The image is displayed, and an operator selects the imaging volume from the displayed image. The pulse sequence used to acquire the k-space data of the scout image may be selected to generate a suitable scout image while requiring minimal acquisition time, such as a single-shot pulse sequence. The scout image may be acquired by another imaging modality, such as but not limited to computed tomography, positron emission tomography and single-photon emission computed tomography. If a non-MR modality is used, the scout image may be acquired so as to be registerable with the MR scanner to be used in subsequent steps of process 300.

Default values of a center frequency and of shim currents for use while imaging the imaging volume are determined at S320. The default values are determined so as to reduce inhomogeneity and/or off-resonance in the $B_0$ field within the imaging volume. S320 may include mapping the $B_0$ field in the imaging volume and determining the default values based on the mapping as is known in the art. In one non-exhaustive example, S320 comprises determining a default center frequency of a $0^{th}$-order shim channel and default shim currents for three $1^{st}$-order linear shim channels implemented by gradient coils, for twelve superconducting shim coils which provide $2^{nd}$-order shimming and $3^{rd}$-order shimming, and for a shim coil array placed near or on the subject.

Figure 4:
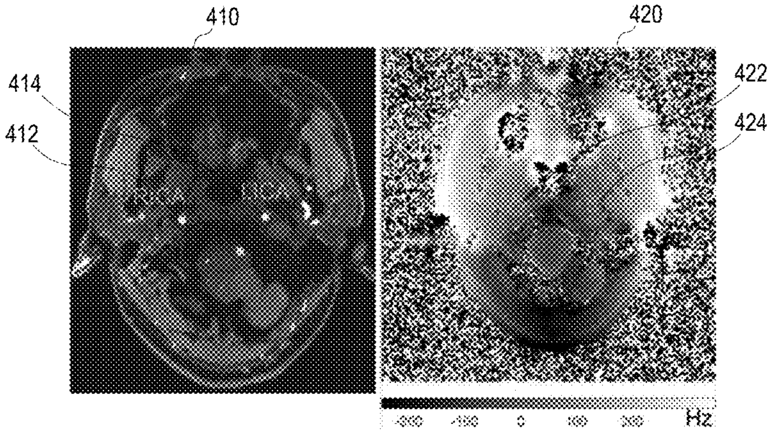
FIG. 4 illustrates a labeling plane and a field map according to some embodiments.

A labeling region associated with the imaging volume is determined at S330. The location of the labeling region is determined to ensure that molecules labeled therein flow into the imaging volume shortly after such labeling. According to some embodiments, S330 includes acquiring an angiographic image of the subject using the MR scanner and determining the labeling region from the angiographic image. FIG. 4 illustrates angiographic image 410 in which the labeling region may be determined as a plane including the right internal carotid artery (RICA) 412 and the left internal carotid artery (LICA) 414.

At S340, the $B_0$ field in the labeling region is determined while the default shim currents are applied to their default shim channels. S340 may comprise acquiring a field map as is known in the art. For example, field map 420 of FIG. 4 represents the $B_0$ field in the labeling region shown in image 410. Also shown are values 422, 424 of the $B_0$ field at locations of RICA 412 and LICA 414, respectively.

S350 includes a determination of an adjusted center frequency and adjusted shim currents of the $1^{st}$-order shim channels. The adjusted frequency and adjusted shim currents are determined so as to reduce off-resonance in the $B_0$ field of the labeling region. The determination may be based on $B_0$ field values 422, 424 of RICA 412 and LICA 414 and assumes concurrent application of the default shim currents of the higher-order shim channels.

Figure 5:
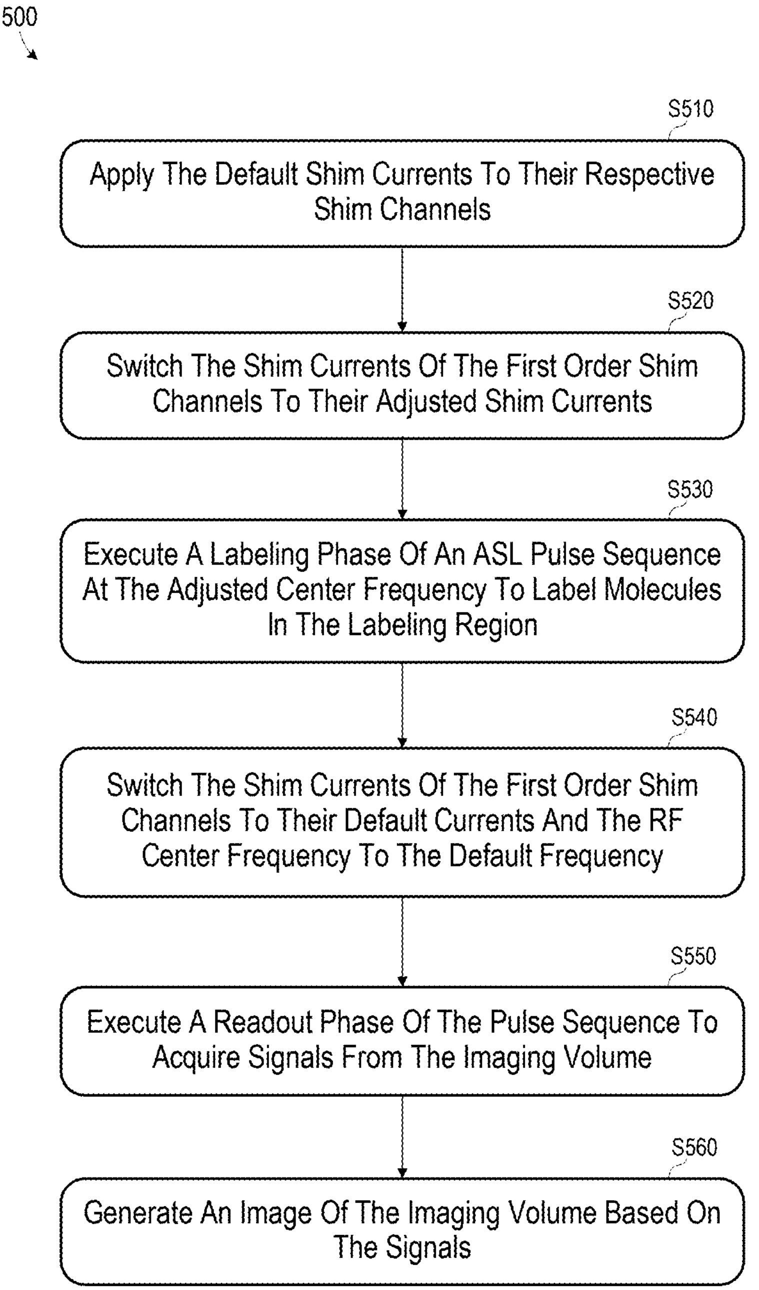
FIG. 5 is a flow diagram of arterial spin labeling imaging using dynamic low-order shimming according to some embodiments.

FIG. 5 is a flow diagram process 500 of arterial spin labeling imaging using dynamic low-order shimming according to some embodiments. At S510, the default shim currents are applied to their respective shim channels.

Next, at S520, the shim currents applied to the $1^{st}$-order shim channels are switched to the adjusted shim currents determined at S350, while the default shim currents remain applied to the higher-order shim channels. As described above, the shim currents applied at S520 are intended to reduce off-resonance in the $B_0$ field of the labeling region.

At S530, a labeling phase of an arterial spin labeling pulse sequence is executed using RF pulses at the adjusted center frequency. The labeling phase is executed while the adjusted and default shim currents are applied to their respective shim channels. Since the center frequency of the RF pulses matches the resonant frequency of the $B_0$ field of the labeling region (or at positions through which blood flows in the labeling region such as RICA 412 and LICA 414), labeling of the molecules in the labeling region proceeds more efficiently than in prior designs. In some embodiments, the labeling phase includes 750 Hanning-shaped 20° RF-pulses each lasting 0.5 msec applied over a 1.5 second period.

The labeling phase of the pulse sequence may include gradient pulses. In a case that the gradient coils are also used for $1^{st}$-order shimming, currents required to produce the gradient pulses are added to any adjusted shim currents applied to the $1^{st}$-order shim channels at S520.

At S540, after execution of the labeling phase, the shim currents of the $1^{st}$-order shim channels are switched to their default currents and the RF center frequency is switched to the default frequency. The switching may occur during a post-labeling period which is intended to allow the now-labeled molecules to flow from the labeling region to the imaging volume.

A readout phase of the pulse sequence is executed at S550 to acquire signals from the imaging volume. During the readout phase, the default shim currents remain applied to their respective shim channels, so as to reduce inhomogeneity and/or off-resonance in the $B_0$ field of the imaging volume. Moreover, RF pulses transmitted and received during the readout phase are tuned to the default center frequency. As mentioned above, the readout phase may comprise an echo-planar imaging pulse sequence, a fast spin echo pulse sequence, a gradient-recalled echo pulse sequence, or any other suitable pulse sequence.

An image of the imaging volume is generated at S560 based on the signals acquired at S540. The image may comprise a two-dimensional or a three-dimensional image. The image may be displayed to an operator. As described above, a difference between the image and an image generated using the same readout pulse sequence and imaging shim channels/shim currents but without a preceding labeling phase may be calculated to generate a unitless perfusion-weighted image.

Figure 6:
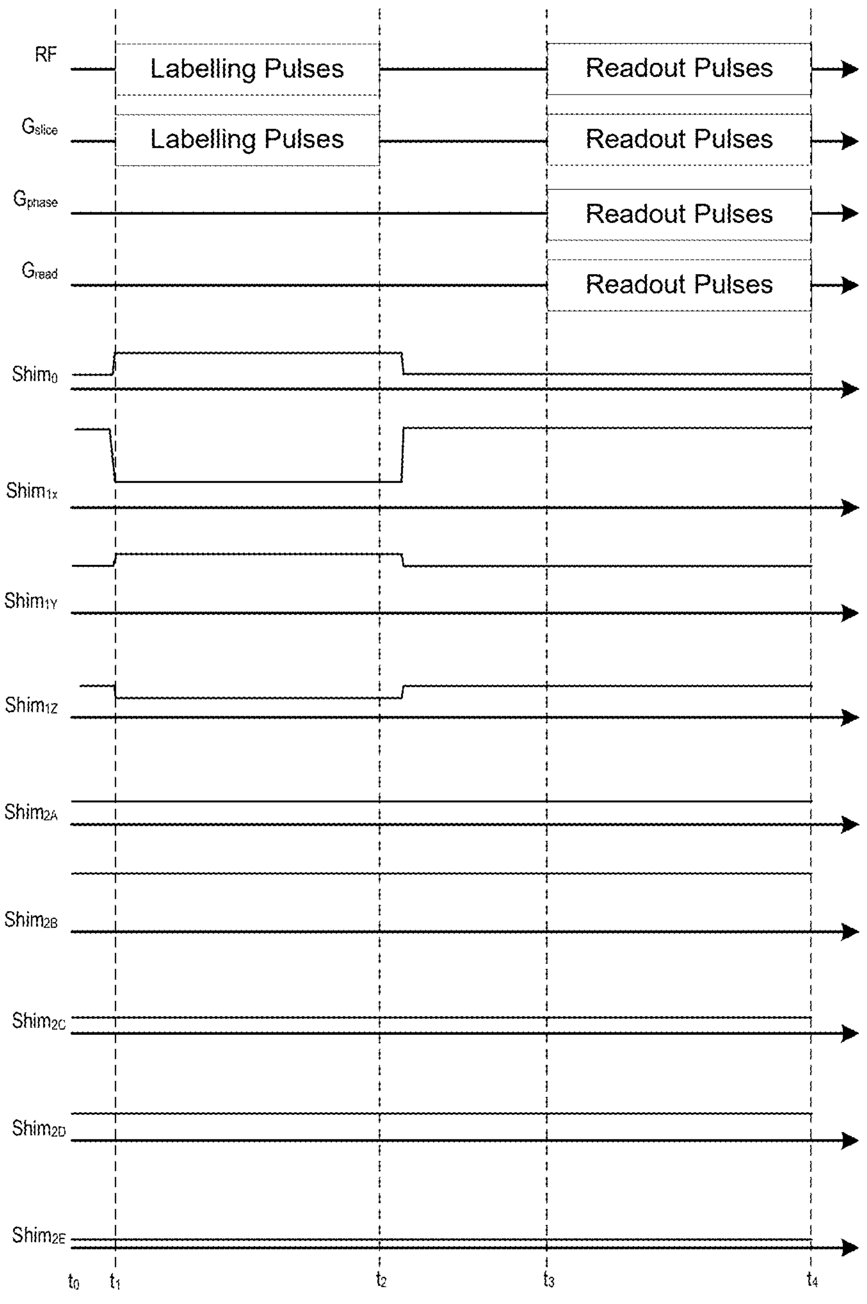
FIG. 6 is a timing diagram of a readout pulse sequence and shim currents for various shim channels according to some embodiments.

FIG. 6 comprises timing diagrams of shim currents for various shim channels according to some embodiments. The illustrated time points $t_0$, $t_1$, $t_2$, $t_3$, $t_4$ correspond to the labeling and readout phases illustrated in FIG. 1. The vertical axis of the $Shim_0$ shim channel timing diagram represents frequency, while the vertical axes of the other shim channel timing diagrams represent current, and the remaining timing diagrams represent voltages over time.

At time $t_0$, default shim currents are applied to $1^{st}$-order shim channels $Shim_{1X}$, $Shim_{1Y}$, and $Shim_{1Z}$ and to $2^{nd}$-order shim channels $Shim_{2A}$, $Shim_{2B}$, $Shim_{2C}$, $Shim_{2D}$ and $Shim_{2E}$, and the $0^{th}$-order shim channel is set to a default center frequency as described above. At time $t_1$, the shim currents are applied to the $1^{st}$-order shim channels are changed to the adjusted shim currents, the default shim currents remain applied to $2^{nd}$-order shim channels $Shim_{2A}$, $Shim_{2B}$, $Shim_{2C}$, $Shim_{2D}$ and $Shim_{2E}$, and the $0^{th}$-order shim channel is set to an adjusted center frequency.

The shim currents and center frequency are held fixed from time $t_1$ to time $t_2$ while a labeling phase of a pulse sequence is executed to label molecules in a labeling region. The labeling phase may include RF pulses and $G_{slice}$ pulses as is known in the art. A post-labeling delay elapses between time $t_2$ and time $t_3$ to allow the now-labeled molecules to flow to an imaging volume. The shim currents applied to the $2^{nd}$-order shim channels $Shim_{2A}$, $Shim_{2B}$, $Shim_{2C}$, $Shim_{2D}$ and $Shim_{2E}$ remain constant during the post-labeling delay. The shim currents applied to $1^{st}$-order shim channels $Shim_0$, $Shim_{1X}$, $Shim_{1Y}$, and $Shim_{1Z}$ are switched from the adjusted shim currents to default shim currents and the center frequency of the $0^{th}$-order shim channel is switched from the adjusted center frequency to a default center frequency between time $t_2$ and time $t_3$.

The MR scanner applies readout pulses suitable to readout signals from the imaging volume between time $t_3$ and time $t_4$, while all the shim currents remain at their default values and the center frequency remains at the default center frequency. The readout pulses may comprise RF pulses, $G_{slice}$ pulses, $G_{phase}$ pulses and $G_{read}$ pulses of an echo-planar imaging pulse sequence, a fast spin echo pulse sequence, a gradient-recalled echo pulse sequence, or any other suitable pulse sequence.

The foregoing diagrams represent logical architectures for describing processes according to some embodiments, and actual implementations may include more or different components arranged in other manners. Other topologies may be used in conjunction with other embodiments. Moreover, each component or device described herein may be implemented by any number of devices in communication via any number of other public and/or private networks. Two or more of such computing devices may be located remote from one another and may communicate with one another via any known manner of network(s) and/or a dedicated connection. Each component or device may comprise any number of hardware and/or software elements suitable to provide the functions described herein as well as any other functions. For example, any computing device used in an implementation of a system according to some embodiments may include a processor to execute program code such that the computing device operates as described herein.

Embodiments described herein are solely for the purpose of illustration. Those in the art will recognize other embodiments may be practiced with modifications and alterations to that described above.

What is claimed is:

1. A system comprising:

a magnet system configured to generate a polarizing magnetic field;

a radio frequency (RF) system to apply an excitation field to the subject and to acquire magnetic resonance (MR) data;

a first-order shim coil;

a second-order shim coil;

a display; and at least one processing unit to execute program code to:

apply a first shim current to the first-order shim coil;

apply a second shim current to the second-order shim coil;

set a center frequency of the RF system to a first center frequency;

execute a labeling phase of an arterial spin labeling pulse sequence while the first shim current is applied to the first-order shim coil, the second shim current is applied to the second-order shim coil, and the center frequency of the RF system is set to the first center frequency;

change the first shim current applied to the first-order shim coil to a third shim current during a post-labeling delay of the pulse sequence;

change the center frequency of the RF system to a second center frequency during the post-labeling delay of the pulse sequence;

execute a readout phase of the arterial spin labeling pulse sequence to acquire first MR data from an imaging volume of a subject while the third shim current is applied to the first-order shim coil, the second shim current is applied to the second-order shim coil, and the center frequency of the RF system is set to the second center frequency;

generate an image based on the first MR data; and display the image on the display.

2. The system of claim 1, the at least one processing unit to execute program code to:

determine a $B_0$ field in a labeling region of the subject while the second shim current is applied to the second-order shim coil; and determine the first shim current and the first center frequency based on the determined $B_0$ field.

3. The system of claim 2, wherein the $B_0$ field is determined at a right internal carotid artery and a left internal carotid artery in the labeling region of the subject, and wherein determination of the first shim current and the first center frequency comprises determination of the first shim current and the first center frequency to reduce off-resonance at the right internal carotid artery and the left internal carotid artery in the labeling region while the second shim current is applied to the second-order shim coil.

4. The system of claim 2, the at least one processing unit to execute program code to:

determine a second $B_0$ field in the imaging volume of the subject; and determine the second shim current, the third shim current and the second center frequency based on the determined second $B_0$ field.

5. The system of claim 4, wherein determination of the second shim current, the third shim current and the second center frequency comprises determination of the second shim current, the third shim current and the second center frequency to reduce off-resonance and inhomogeneity of the second $B_0$ field in the imaging volume.

6. The system of claim 1, further comprising:

a second first-order shim coil and a third first-order shim coil;

a second second-order shim coil, a third second-order shim coil; a fourth second-order shim coil, and a fifth second-order shim coil;

the at least one processing unit to execute program code to:

execute the labeling phase of the arterial spin labeling pulse sequence while the first shim current is applied to the first-order shim coil, the second shim current is applied to the second-order shim coil, a fourth shim current is applied to the second first-order shim coil, a fifth shim current is applied to the third first-order shim coil, a sixth shim current is applied to the second second-order shim coil, a seventh shim current is applied to the third second-order shim coil, an eighth shim current is applied to the fourth second-order shim coil, a ninth shim current is applied to the fifth second-order shim coil and the center frequency of the RF system is set to the first center frequency; and execute the readout phase of the arterial spin labeling pulse sequence to acquire the first MR data from the subject while the third shim current is applied to the first-order shim coil, the second shim current is applied to the second-order shim coil, a tenth shim current is applied to the second first-order shim coil, an eleventh shim current is applied to the third first-order shim coil, the sixth shim current is applied to the second second-order shim coil, the seventh shim current is applied to the third second-order shim coil, the eighth shim current is applied to the fourth second-order shim coil, the ninth shim current is applied to the fifth second-order shim coil and the center frequency of the RF system is set to the second center frequency.

7. The system of claim 6, the at least one processing unit to execute program code to:

determine a $B_0$ field in a labeling region of the subject while the second shim current is applied to the second-order shim coil, the sixth shim current is applied to the second second-order shim coil, the seventh shim current is applied to the third second-order shim coil, the eighth shim current is applied to the fourth second-order shim coil, and the ninth shim current is applied to the fifth second-order shim coil; and determine the first shim current, the fourth shim current, the fifth shim current and the first center frequency based on the determined $B_0$ field.

8. The system of claim 7, wherein the $B_0$ field is determined at a right internal carotid artery and a left internal carotid artery in the labeling region of the subject, and wherein determination of the first shim current, the fourth shim current, the fifth shim current and the first center frequency comprises determination of the first shim current, the fourth shim current, the fifth shim current and the first center frequency to reduce off-resonance at the right internal carotid artery and the left internal carotid artery in the labeling region while the second shim current is applied to the second-order shim coil, the sixth shim current is applied to the second second-order shim coil, the seventh shim current is applied to the third second-order shim coil, the eighth shim current is applied to the fourth second-order shim coil, and the ninth shim current is applied to the fifth second-order shim coil.

9. The system of claim 7, the at least one processing unit to execute program code to:

determine a second $B_0$ field in the imaging volume of the subject; and determine the second shim current, the third shim current, the sixth shim current, the seventh shim current, the eighth shim current, the ninth shim current, the tenth shim current, the eleventh shim current and the second center frequency based on the determined second $B_0$ field, wherein determination of the second shim current, the third shim current, the sixth shim current, the seventh shim current, the eighth shim current, the ninth shim current, the tenth shim current, the eleventh shim current and the second center frequency comprises determination of the second shim current, the third shim current, the sixth shim current, the seventh shim current, the eighth shim current, the ninth shim current, the tenth shim current, the eleventh shim current and the second center frequency to reduce off-resonance and inhomogeneity of the second $B_0$ field in the imaging volume.

10. A method comprising:

applying respective first shim currents to a plurality of first-order shim coils of an MR scanner;

applying respective second shim currents to a plurality of second-order shim coils of the MR scanner;

setting a center frequency of an RF system of the MR scanner to a first center frequency;

executing a labeling phase of an arterial spin labeling pulse sequence while the respective first shim currents are applied to the plurality of first-order shim coils, the respective second shim currents are applied to the plurality of second-order shim coils, and the center frequency of the RF system is set to the first center frequency;

during a post-labeling delay of the arterial spin labeling pulse sequence, switching the respective first shim currents applied to the plurality of first-order shim coils to respective third shim currents and switching the center frequency of the RF system to a second center frequency;

executing a readout phase of the arterial spin labeling pulse sequence to acquire first MR data from an imaging volume of a subject while the respective third shim currents are applied to the plurality of first-order shim coils, the respective second shim currents are applied to the plurality of second-order shim coils, and the center frequency of the RF system is set to the second center frequency; and generating an image based on the first MR data.

11. The method of claim 10, further comprising:

applying a $B_0$ field to a subject using a main magnet of the MR scanner;

determining the respective third shim currents for each of the plurality of first-order shim coils and the respective second shim currents for each of the plurality of second-order shim coils based on the $B_0$ field in an imaging volume of the subject;

applying, to each of the plurality of second-order shim coils, their respective second shim currents;

determining a second $B_0$ field in a labeling region adjacent to the imaging volume while the respective second shim currents are applied to each of the plurality of second-order shim coils; and determining the respective first shim currents and the first center frequency based on the determined second $B_0$ field.

12. The method of claim 11, wherein the second $B_0$ field is determined at a right internal carotid artery and a left internal carotid artery in the labeling region of the subject, and wherein determining the first shim currents and the first center frequency comprises determining the first shim currents and the first center frequency to reduce off-resonance of the second $B_0$ field at the right internal carotid artery and the left internal carotid artery in the labeling region while the second shim currents are applied to the plurality of second-order shim coils.

13. The method of claim 12, wherein determining the second shim currents, the third shim currents and the second center frequency comprises determining the second shim currents, the third shim currents and the second center frequency to reduce off-resonance and inhomogeneity of the $B_0$ field in the imaging volume.

14. A non-transitory computer-readable medium storing program code executable by at least one processing unit to cause a computing system to:

instruct application of respective first shim currents to a plurality of first-order shim coils of an MR scanner;

instruct application of respective second shim currents to a plurality of second-order shim coils of the MR scanner;

instruct application setting of a center frequency of an RF system of the MR scanner to a first center frequency;

instruct the MR scanner to execute a labeling phase of an arterial spin labeling pulse sequence while the respective first shim currents are applied to the plurality of first-order shim coils, the respective second shim currents are applied to the plurality of second-order shim coils, and the center frequency of the RF system is set to the first center frequency;

during a post-labeling delay of the arterial spin labeling pulse sequence, instruct switching of the respective first shim currents applied to the plurality of first-order shim coils to respective third shim currents and switching of the center frequency of the RF system to a second center frequency;

instruct the MR scanner to execute a readout phase of the arterial spin labeling pulse sequence to acquire first MR data from an imaging volume of a subject while the respective third shim currents are applied to the plurality of first-order shim coils, the respective second shim currents are applied to the plurality of second-order shim coils, and the center frequency of the RF system is set to the second center frequency; and generate an image based on the first MR data.

15. The non-transitory computer-readable medium of claim 14, the program code executable by at least one processing unit to cause a computing system to:

instruct a main magnet of the MR scanner to apply a $B_0$ field to a subject;

determine the respective third shim currents for each of the plurality of first-order shim coils and the respective second shim currents for each of the plurality of second-order shim coils based on the $B_0$ field in an imaging volume of the subject;

instruct application, to each of the plurality of second-order shim coils, of their respective second shim currents;

determine a second $B_0$ field in a labeling region adjacent to the imaging volume while the respective second shim currents are applied to each of the plurality of second-order shim coils; and determine the respective first shim currents and the first center frequency based on the determined second $B_0$ field.

16. The non-transitory computer-readable medium of claim 15, wherein the second $B_0$ field is determined at a right internal carotid artery and a left internal carotid artery in the labeling region of the subject, and wherein determining the first shim currents and the first center frequency comprises determining the first shim currents and the first center frequency to reduce off-resonance of the second $B_0$ field at the right internal carotid artery and the left internal carotid artery in the labeling region while the second shim currents are applied to the plurality of second-order shim coils.

17. The non-transitory computer-readable medium of claim 16, wherein determining the second shim currents, the third shim currents and the second center frequency comprises determining the second shim currents, the third shim currents and the second center frequency to reduce off-resonance and inhomogeneity of the $B_0$ field in the imaging volume.

* * * * *